(12) United States Patent
Ueoka

(10) Patent No.: US 8,723,141 B2
(45) Date of Patent: May 13, 2014

(54) LINE SENSOR UNIT AND AUTOMATIC TRANSACTION APPARATUS

(71) Applicant: Fujitsu Frontech Limited, Tokyo (JP)

(72) Inventor: Tadashi Ueoka, Tokyo (JP)

(73) Assignee: Fujitsu Frontech Limited, Tokyo (JP)

( * ) Notice: Subject to any disclaimer, the term of this patent is extended or adjusted under 35 U.S.C. 154(b) by 0 days.

(21) Appl. No.: 13/950,941

(22) Filed: Jul. 25, 2013

(65) Prior Publication Data

US 2013/0306879 A1 Nov. 21, 2013

Related U.S. Application Data

(63) Continuation of application No. PCT/JP2011/058349, filed on Mar. 31, 2011.

(51) Int. Cl.
*G01N 21/64* (2006.01)
*G07D 7/12* (2006.01)

(52) U.S. Cl.
CPC . *G01N 21/64* (2013.01); *G07D 7/12* (2013.01)
USPC ............... 250/458.1; 250/556; 250/578.1

(58) Field of Classification Search
CPC ................................. G01N 21/64; G07D 7/12
USPC ................................. 250/458.1, 556
See application file for complete search history.

(56) References Cited

U.S. PATENT DOCUMENTS

| 5,955,741 | A * | 9/1999 | Kayani .................... 250/559.11 |
| 6,994,201 | B2 * | 2/2006 | Yu et al. ......................... 194/207 |
| 2007/0246654 | A1 * | 10/2007 | Chien et al. ................ 250/341.8 |
| 2008/0292360 | A1 | 11/2008 | Hirai |
| 2010/0102234 | A1 * | 4/2010 | Hamasaki et al. ......... 250/341.7 |
| 2011/0052085 | A1 | 3/2011 | Ikari et al. |

FOREIGN PATENT DOCUMENTS

| JP | 2001-119530 | 4/2001 |
| JP | 2003-006701 A | 1/2003 |
| JP | 2008-287145 | 11/2008 |
| JP | 2009-37418 | 2/2009 |
| JP | 2011-48677 | 3/2011 |

OTHER PUBLICATIONS

Int'l. Search Report issued in Int'l. App. No. PCT/JP2011/058349, Jun. 21, 2013.

* cited by examiner

*Primary Examiner* — David Porta
*Assistant Examiner* — Gisselle Gutierrez
(74) *Attorney, Agent, or Firm* — Greer Burns & Crain Ltd.

(57) ABSTRACT

A line sensor unit includes: a first light source configured to emit excitation light that excites a fluorescent substance; a second light source configured to emit non-excitation light that does not excite the fluorescent substance; a line sensor configured to receive light from a medium obtained by irradiating the medium with the excitation light or the non-excitation light; a light-emitting unit, which is excited upon receipt of the excitation light, configured to emit light responsive to the excitation light, the emitted light being incident on the line sensor; and a light-shielding unit, which is provided on a side opposite to a line-sensor side of the light-emitting unit, configured to block light advancing from the light-emitting unit to the medium.

4 Claims, 15 Drawing Sheets

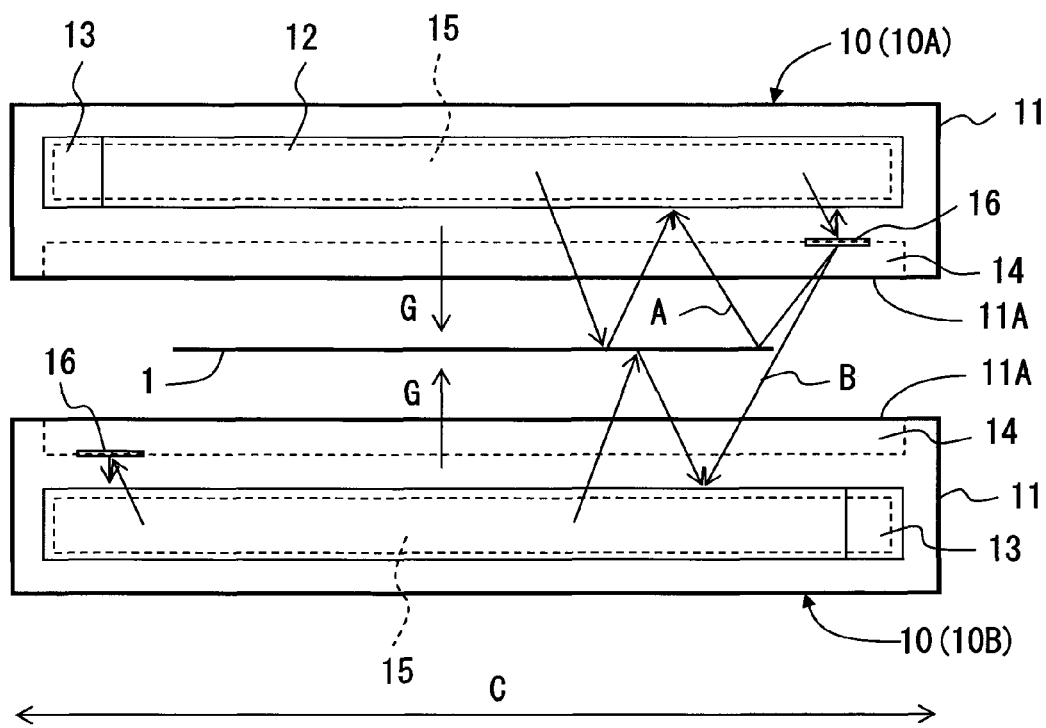
F I G. 1A

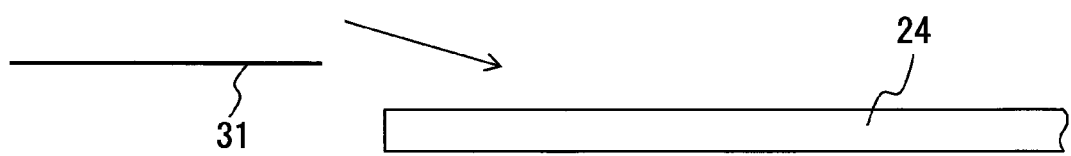
F I G. 4 A

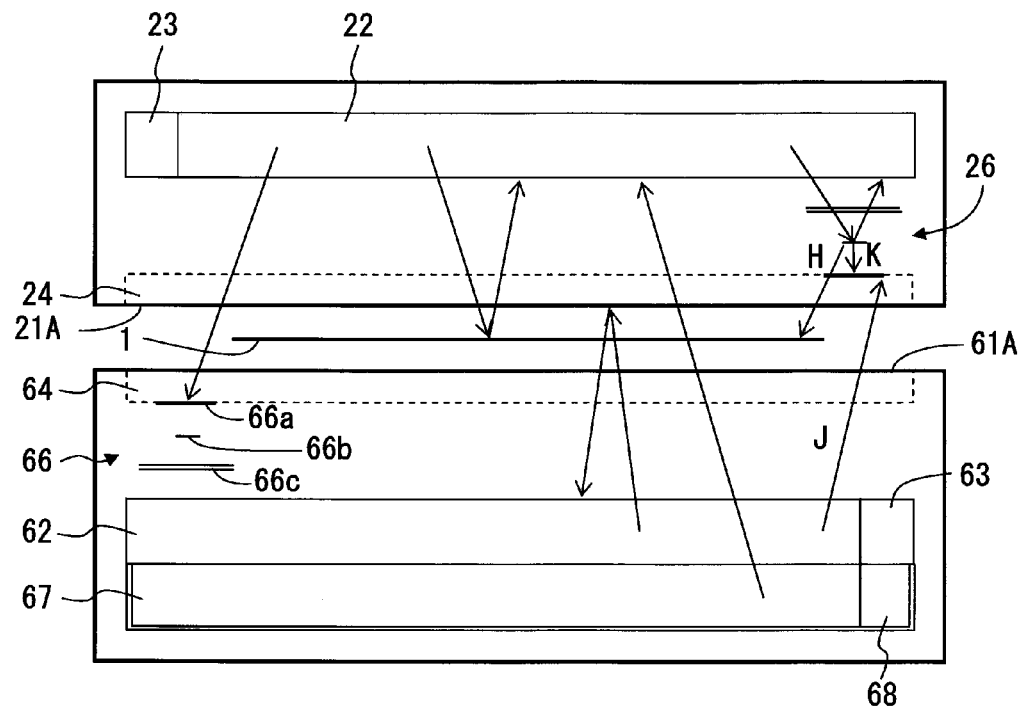
F I G. 6 A

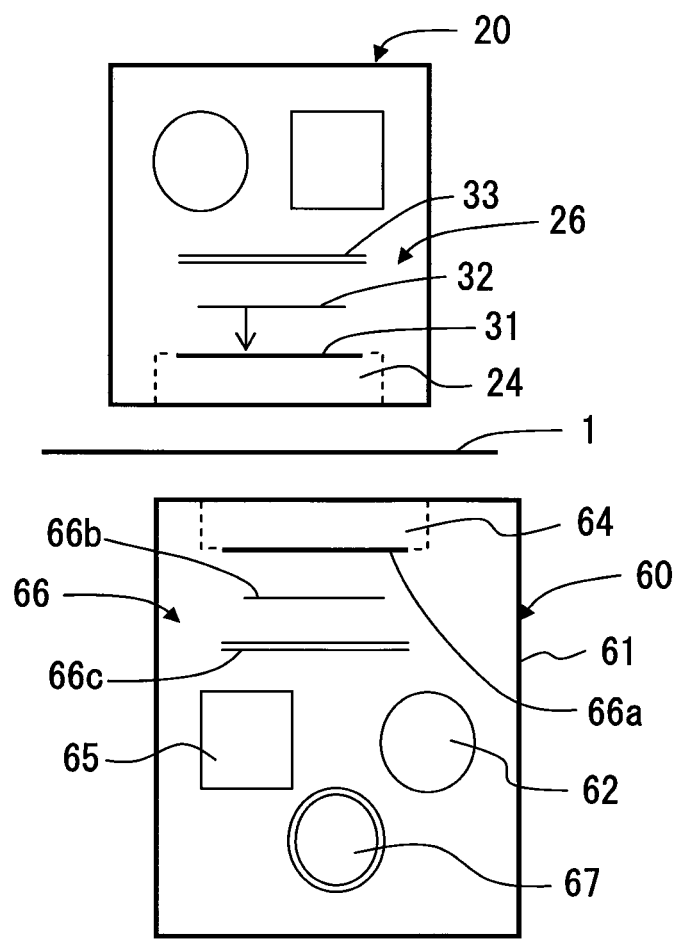
F I G. 6 B

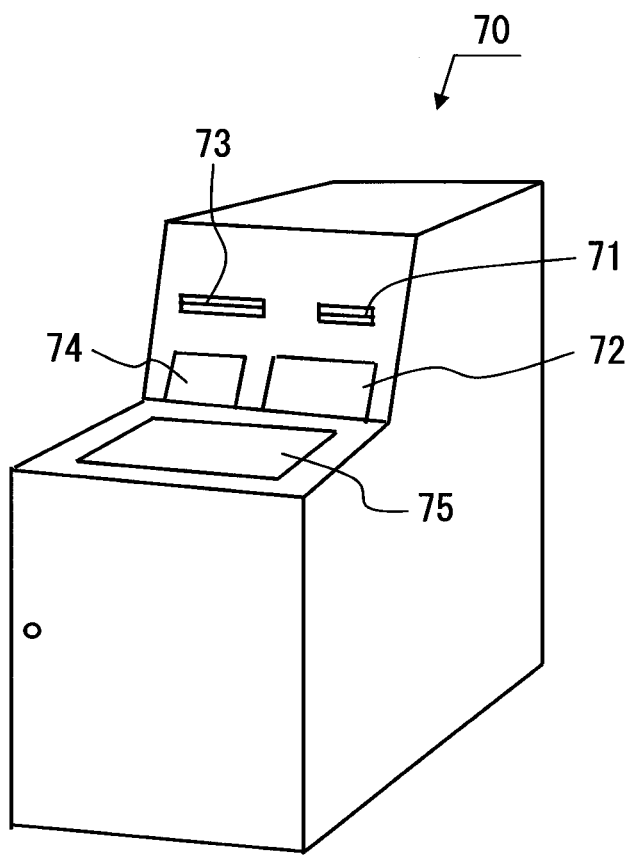
F I G. 7

LINE SENSOR UNIT AND AUTOMATIC TRANSACTION APPARATUS

CROSS-REFERENCE TO RELATED APPLICATION

This application is a continuation application of International Application PCT/JP2011/058349 filed on Mar. 31, 2011 and designated the U.S., the entire contents of which are incorporated herein by reference.

FIELD

The embodiments discussed herein are related to a technology for reading an image of a medium with a line sensor by using light that excites a fluorescent substance and light that does not excite the fluorescent substance.

BACKGROUND

Line sensors provided with a plurality of light receiving elements that convert incident light into an electronic signal are widely used to, for example, read an image formed on a medium such as a sheet. The reading is typically performed by irradiating the medium with light emitted from a light source and causing light from the medium obtained via the irradiation to be incident on the line sensor. While the reading is being performed, the position relationship between the medium and the line sensor is sequentially changed so that the image of the entire medium can be read.

Even though the image of the same medium is read by causing the light source to emit light under the same condition, the level of a signal output from each light receiving element of the line sensor varies in accordance with, for example, environmental temperature and secular changes in the light source and the light receiving elements. Thus, to avoid a change in a signal level caused by, for example, environmental temperature and a secular change, requirements to drive and cause the light source to emit light are adjusted. In general, in the adjusting method, the light source is caused to emit light under the same condition, the emitted light is reflected from a reflector prepared in advance, the signal level of the light receiving element obtained by causing reflected light from the reflector to be incident on the line sensor is compared with a signal level prepared in advance, and the comparison result is obtained. Using such an adjustment method to adjust the requirements to drive the light source may suppress the change in the signal level of the light receiving elements of the line sensor that would be made by, for example, environmental temperature or a secular change.

Media from which an image is read using the line sensor include banknotes. Some banknotes include a fluorescent substance to prevent circulation of forged notes. The fluorescent substance is applied to a banknote via, for example, printing with fluorescent ink. The fluorescent substance applied to a banknote via printing with fluorescent ink emits light when it is irradiated with excitation light such as ultraviolet rays. Thus, the portion of a fluorescent-substance-including banknote that emits light upon irradiation with excitation light allows a visual inspection to be performed to determine whether the banknote is real or false. Recently, without a visual inspection, a portion that emits light upon irradiation with excitation light has also been able to be read by a line sensor to automatically determine whether the banknote is real or false (patent document 3).

Patent document 1: Japanese Laid-open Patent Publication No. 2001-119530

Patent document 2: Japanese Laid-open Patent Publication No. 2008-287145

Patent document 3: Japanese Laid-open Patent Publication No. 2009-37418

SUMMARY

According to an aspect of the embodiments, a system to which the present invention has been applied includes: a first light source that emits excitation light that excites a fluorescent substance; a second light source that emits non-excitation light that does not excite the fluorescent substance; a line sensor that receives light from a medium obtained by irradiating the medium with excitation light or non-excitation light; a light-emitting unit that is excited upon receipt of excitation light and that emits light responsive to the excitation light, the emitted light being incident on the line sensor; and a light-shielding unit that is provided on a side opposite to the line-sensor side of the light-emitting unit and that blocks light from the light-emitting unit.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 1A illustrates an exemplary configuration possibly achieved on the assumption that the images of both sides of a medium are each read by a line sensor (a front view of a line sensor unit).

FIG. 4A illustrates a method for setting up the reflector.

FIG. 6A illustrates an exemplary configuration in which the images of both sides of a medium are read using the line sensor unit in accordance with the embodiment (a front view of the line sensor unit).

FIG. 6B illustrates an exemplary configuration in which the images of both sides of a medium are read using the line sensor unit in accordance with the embodiment (a side view of the line sensor unit).

FIG. 7 is an external view of an automatic transaction apparatus in accordance with the embodiment.

DESCRIPTION OF EMBODIMENTS

According to a study by the inventor, to judge a banknote, damages, dirt, and so on are typically checked in addition to making a determination of whether the banknote is real or false. It is difficult to accurately check damage or dirt through image reading with a fluorescent substance using excitation light. Thus, in order to perform a process of judging a fluorescent-substance-including banknote that includes the checking for, for example, damage and dirt in addition to making a determination of whether the banknote is real or false, image reading with non-excitation light such as white light needs to be performed in addition to image reading with a fluorescent substance using excitation light.

To read, as an image, a fluorescent substance emitting light on a medium with a line sensor, a light source that emits excitation light to excite the fluorescent substance (hereinafter referred to as an "excitation-light source") is used. Thus, in order to judge a fluorescent-substance-including banknote, an excitation-light source and a light source that emits non-excitation light (hereinafter referred to as a "non-excitation-light source") are needed.

In general, product development requires cost reductions. In view of this requirement, a single line sensor may perform both image reading with excitation light and image reading with non-excitation light. When one line sensor is used like this, the excitation-light source and the non-excitation-light source are provided within a relatively narrow area.

Also, for the excitation-light source, the requirements for driving need to be adjusted in accordance with environmental temperature or secular changes. To adjust the requirements to drive the excitation-light source, a luminous body that emits light upon irradiation with excitation light needs to be used instead of the aforementioned reflector. Such a luminous body has a time period from the end of irradiation with excitation light to the extinction of light (emission lifetime). Thus, when image reading with excitation light that follows image reading with excitation light is performed under a condition in which the excitation-light source and the non-excitation-light source are provided within a relatively narrow area, light emitted from the luminous body may possibly irradiate a portion of the banknote.

Differences in the amount of irradiation light between positions on a banknote create an obstacle to accurate reading of the image of the banknote. Accordingly, in order to accurately read an image with non-excitation light, it is important to further limit the influence of image reading with excitation light.

Figure 1B:
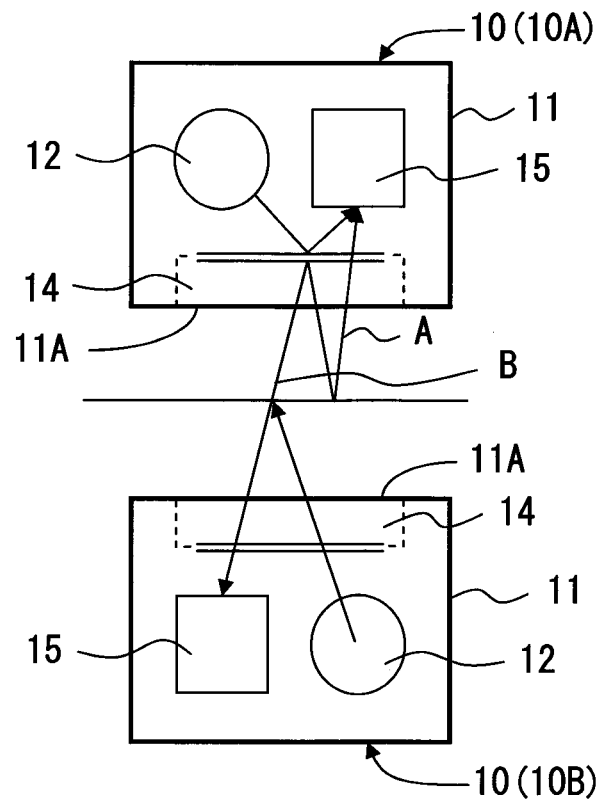
FIG. 1B illustrates an exemplary configuration possibly achieved on the assumption that the images of both sides of a medium are each read by a line sensor (a side view of a line sensor unit).
Figure 1C:
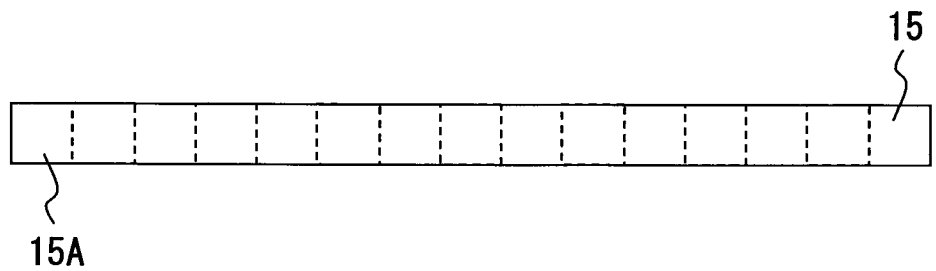
FIG. 1C illustrates a configuration of a line sensor.

First, with reference to FIG. 1A to FIG. 1C, an exemplary configuration will be described that allows images of a medium to be consecutively read with excitation light and non-excitation light by using one line sensor. FIG. 1A and FIG. 1B illustrate an exemplary configuration possibly achieved on the assumption that the images of both sides of a medium 1 are each read. FIG. 1A illustrates the exemplary configuration viewed from an orthogonal direction that is orthogonal to the longer direction of the medium 1, i.e., a front view of line sensor units 10; FIG. 1B illustrates the exemplary configuration viewed from the longer direction, i.e., a side view of the line sensor units. FIG. 1C illustrates a configuration of the line sensor.

In FIG. 1A and FIG. 1B, numeral 10 indicates the line sensor units. A line sensor unit 10A is provided for reading an image of the front side of the medium 1, and a line sensor unit 10B is provided for reading an image of the back side of the medium 1. As illustrated in FIG. 1A and FIG. 1B, the line sensor units 10 (10A and 10B) have the same configuration, wherein a light guide plate 12, a light-source unit 13, a cover 14, a line sensor 15, and a light-emitting reflector 16 are stored in a case 11. Accordingly, the line sensor units 10 are achieved as one unit provided with functions to read an image on the medium 1.

The case 11, which is shaped as a square pole, includes an opening 11A on one of the four surfaces extending along the longer direction (arrow C). The opening 11A of the line sensor 10A and the opening 11A of the line sensor 10B, which are opposite to each other, face a transportation path in which the medium 1 is inserted. The cover 14 is a transparent member that covers the opening 11A and that prevents dust and so on from entering the inside through the opening 11A. The light-emitting reflector 16 is attached to one end of the longer direction of the cover 14 by, for example, an adhesive.

The light-source unit 13 includes at least: an excitation-light source that emits, for example, ultraviolet rays, i.e., a type of excitation light; and a non-excitation-light source that emits, for example, white light. Light from each light source is incident on the light guide plate 12 and is radiated in the direction of arrow G from the entirety of the longer direction of the light guide plate 12 (arrow C) toward the cover 14. In fact, the light guide plate 12 is stored in the case 11 in a manner such that light radiated from the light guide plate 12 is radiated from only the side facing the cover 14. The light guide plate 12 is stored in, for example, a case that includes an opening on only the cover 14 side.

The line sensor 15 includes many light receiving elements 15A arranged along the longer direction (arrow C) of the medium 1, as illustrated in FIG. 1C. Each of the light receiving elements 15A is positioned so that it can receive light from the cover 14 side. Accordingly, an image on the medium 1 is read when light emitted from any of the light sources of the light-source unit 13 follows the route of the light guide plate 12→the cover 14→the medium 1→the cover 14→the line sensor 15 and is incident on the line sensor 15.

The image reading from the medium 1 with excitation light and non-excitation light using the line sensor units 10 having the aforementioned configuration may be achieved by, for example, reading the image with the emission of excitation light and reading the image with the emission of non-excitation light while sequentially changing the position relationship between the line sensor units 10 and the medium 1. In such a reading method, the entirety of the medium 1 is shifted once with respect to the line sensor units 10 in the direction of arrow F, so that both the reading of the image of the entirety of the medium 1 with excitation light and the reading of the image of the entirety of the medium 1 with non-excitation light can be performed. As a result, using such a reading method allows image reading to be performed at a higher speed than in a situation in which image reading with excitation light and image reading with non-excitation are separately performed.

At one end within the case 11 of the longer direction of the line sensor unit 10A (arrow C), the light-emitting reflector 16, which is parallel to the cover 14, is provided at the other end of the longer direction (arrow C) of the line sensor 10A opposite to the light-source unit 13.

When the non-excitation-light source emits light, the light-emitting reflector 16 reflects and causes non-excitation light radiated via the light guide plate 12 to be incident on the line sensor 15. When the excitation-light source emits light, the light-emitting reflector 16 is excited by excitation light radiated from the light guide plate 12, thereby emitting light. The light radiated by the light emission is incident on the line sensor 15. Accordingly, the light-emitting reflector 16 is provided to address, for example, environmental temperatures and secular changes in each light source provided at the light-source unit 13 and each of the light receiving elements 15A of the line sensor 15. In comparison with a situation in which reflection of non-excitation light and light emission caused by irradiation with excitation light are achieved by different members, causing the light-emitting reflector 16 to reflect non-excitation light and to emit light upon irradiation with excitation light may achieve, for example, a reduction in the number of parts leading to a reduction in the cost of fabrication.

After the irradiation with excitation light ends, the light-emitting reflector 16, which has been excited, emits light until the emission life time period elapses. When the light emitted by the light-emitting reflector 16 follows the path indicated by arrow A in FIG. 1A and FIG. 1B, this light is incident on the line sensor 15. Accordingly, when an image of the medium 1 is read by causing the non-excitation-light source to emit light just after the excitation-light source is caused to emit light, the amount of light with which the medium 1 is irradiated varies with position. Such a variation in the amount of light that depends on a position is not desirable to accurately read an image on the medium 1.

To read images of both sides of the medium 1, light emitted by the light-emitting reflector 16 follows the path indicated by arrow B in FIG. 1A and FIG. 1B and enters the line sensor 15 of the line sensor unit 10B (located below the medium 1), i.e., another line sensor unit facing the line sensor unit 10A. In this way, the light that follows the path indicated by arrow B also interferes with accurate reading of an image on the medium 1.

The light-emitting reflector 16 is irradiated with light emitted from one or more of the light sources of the light-source unit 13. As a result, after the light emission from the excitation-light source ends, in the reading of an image with non-excitation light performed before the emission life time period of the light-emitting reflector 16 elapses, accurate image reading is interfered with by light emitted from the light-emitting reflector 16. Accordingly, when a member such as the light-emitting reflector 16 that emits light for a certain period upon irradiation with excitation light is used to deal with, for example, environmental temperatures and secular changes, the emitted light that continues for the certain period makes an obstacle to accurate reading of an image. The present embodiment avoids an occurrence of such a fault. In the following, embodiments of the present invention will be described in detail with reference to the drawings.

Figure 2:
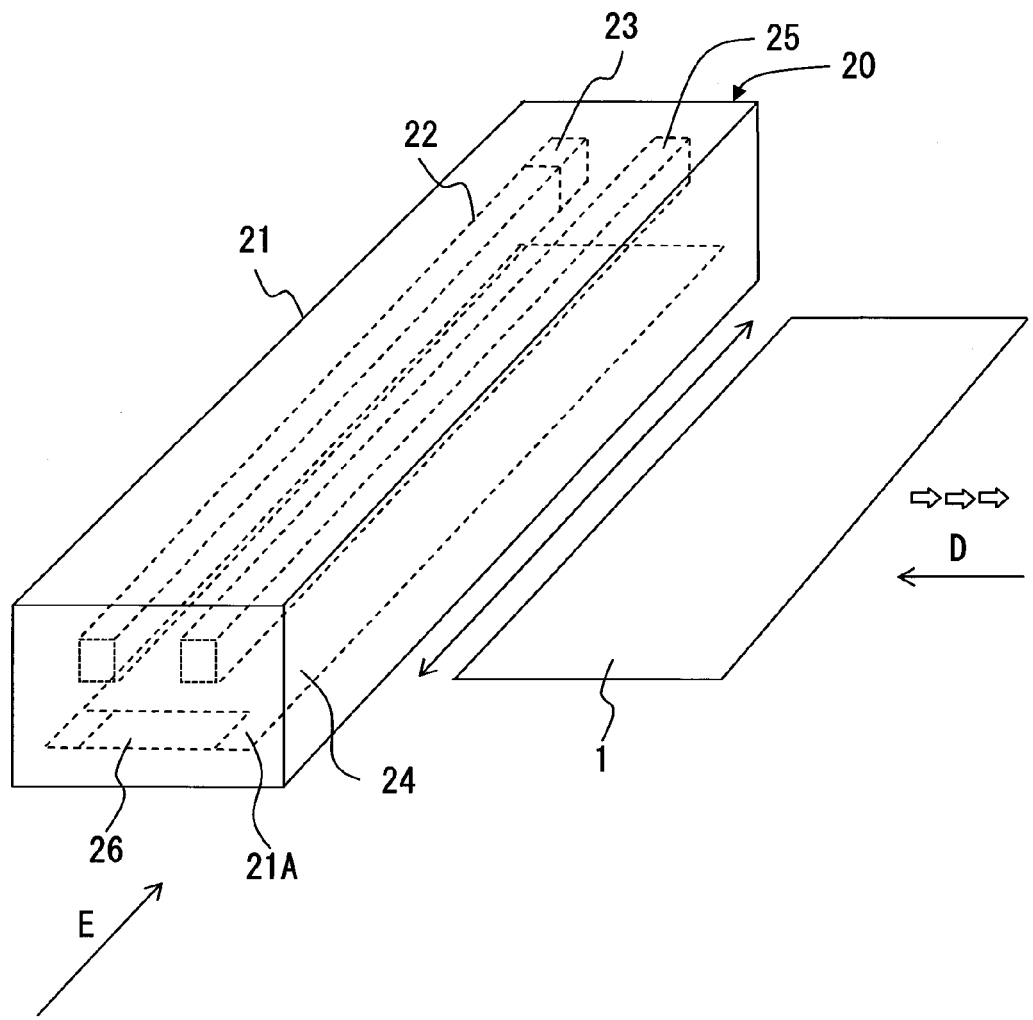
FIG. 2 illustrates a perspective view of a configuration of a line sensor unit in accordance with the embodiment.

FIG. 2 illustrates a perspective view of a configuration of a line sensor unit in accordance with the embodiment. The line sensor unit, i.e., a line sensor unit 20, has a function that irradiates the medium 1 with light and that converts light obtained from the irradiated medium 1 into an electrical signal. Such a function is stored within a case 21, so a high attachment characteristic is achieved for attachment to an apparatus to which image reading functions are to be attached.

As illustrated in FIG. 2, the case 21, which is shaped as a square pole, includes an opening on one of the four surfaces extending along the longer direction of the medium 1 (arrow C). An opening 21A of the line sensor unit 20 faces a transportation path in which the medium 1 is inserted. A cover 24, which prevents dust and so on from entering the inside, is provided at the opening 21A. A light guide plate 22, a light source unit 23, a line sensor 25, and a reflector 26 are stored within a space formed by the cover 24 and the case 21.

The light source unit 23 includes at least: an excitation-light source that emits, for example, ultraviolet rays, i.e., a type of excitation light; and a non-excitation-light source that emits, for example, white light. The light sources are, for example, LEDs (Light Emitting Diodes). Light from each light source is incident on the light guide plate 22 and is radiated from the entirety of the longer direction of the light guide plate 12 (the direction of arrow C) toward the cover 24. In fact, the light guide plate 22 is stored in the case 21 in a manner such that light radiated from the light guide plate 22 is radiated from only the side facing the cover 24. The light guide plate 22 is stored in, for example, the case 21 that includes an opening on only the cover 24 side.

The line sensor 25 includes many light receiving elements 15A arranged along the longer direction (the direction of arrow C) of the medium 1. Each of the light receiving elements 15A is positioned so that it can receive light from the cover 24 side. Accordingly, an image on the medium 1 is read when light emitted from any of the light sources of the light-source unit 23 follows the route of the light guide plate 22→the cover 24→the medium 1→the cover 24→the line sensor 25 and is incident on the line sensor 25.

When the non-excitation-light source emits light, the reflector 26 reflects and causes non-excitation light radiated via the light guide plate 22 to be incident on the line sensor 25. When the excitation-light source emits light, the reflector 26 is excited by excitation light radiated from the light guide plate 22, thereby emitting light. The light radiated by the light emission is incident on the line sensor 25. Simultaneously, the light is also incident on the medium side. Accordingly, the reflector 26 is provided to address, for example, environmental temperatures and secular changes in each light source provided at the light-source unit 23 and each of the light receiving elements of the line sensor 15. Since the reflector 26 is not used in the reading of an image of the medium 1, the reflector 26 is provided at one end of the longer direction of the cover 24 (arrow C).

More particularly, at one end within the case 21 of the longer direction of the line sensor unit 20 (arrow C), the reflector 26, which is parallel to the cover 14, is provided at the other end of the longer direction (arrow C) of the line sensor 10A opposite to the light-source unit 13.

The light source may be one slim light source such as a fluorescent lamp. The light source may include a plurality of fluorescent elements arranged along the longer direction of the line sensor unit 20 (arrow C). In this example, descriptions have been given on the assumption that the medium is read for the longer direction of the medium (arrow C), but reading for the shorter direction of the medium may be similarly performed.

Figure 3:
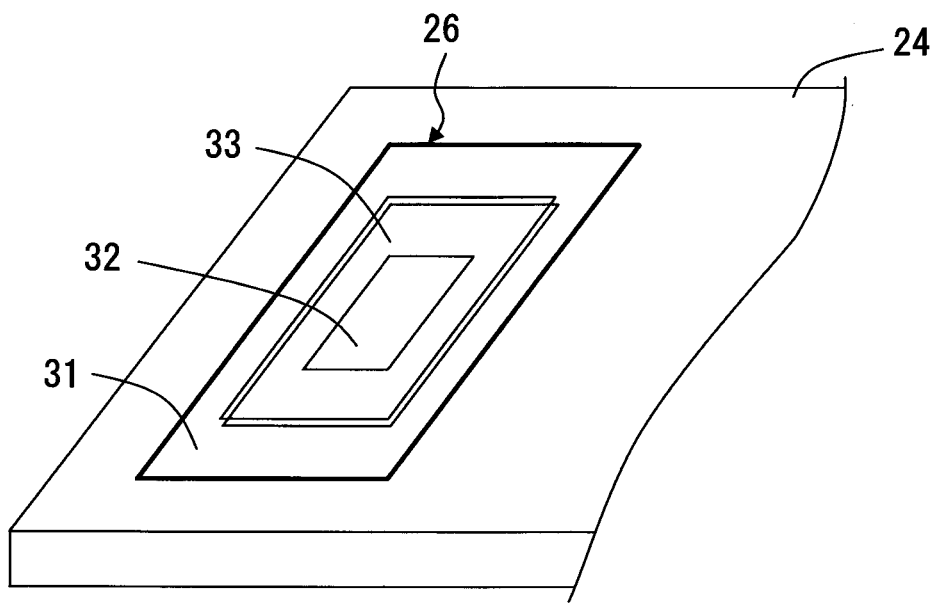
FIG. 3 illustrates a configuration of a reflector.
Figure 4B:
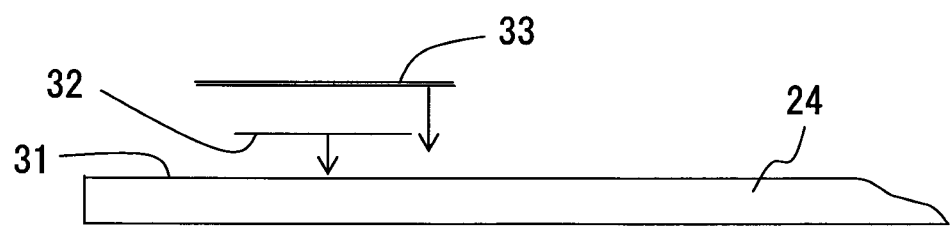
FIG. 4B illustrates a method for setting up the reflector.

FIG. 3 illustrates a configuration of a reflector. FIG. 4A and FIG. 4B illustrate a method for setting up the reflector.

As illustrated in FIG. 3, the reflector 26 includes a light shield 31, a light-emitting reflector 32, and a transparent moisture-resistant material 33. The light shield 31, which blocks light, is provided on a side opposite to the line-sensor side and has a planar shape.

An upright wall may be provided around the light shield 31 so that surrounding light can be blocked more effectively.

The light shield 31 blocks light from the reflector 26 going to the medium 1.

As illustrated in FIG. 6A, the light-emitting reflector 32 is irradiated with light radiated from the line sensor unit 20. In addition, light reflected from the light-emitting reflector 32 may block light H and light K, with which the medium 1 would be irradiated. Light from another luminous body, e.g., light radiated from the line sensor unit 60 on the opposite side when the line sensor units 20 and 60 sandwich the medium 1 from above and below as illustrated in FIG. 6A, may block light J, with which the light-emitting reflector 32 on the opposite side would be irradiated.

The light-emitting reflector 32 and the transparent moisture-resistant material 33 also have a planar shape. The light-emitting reflector 32 reflects non-excitation light and emits light in response to excitation light. The transparent moisture-protection material 33 protects the light-emitting reflector 32 from moisture without blocking light with which the light-emitting reflector 32 is irradiated or light from the light-emitting reflector 32. Accordingly, the reflector 26 is configured in a manner such that the light shield 31, the light-emitting reflector 32, and the transparent moisture-resistance material 33 are stacked in this order with the light shield 31 being the closest to the cover 24. The area of the surface on which the reflector 26 is provided at the cover 24 satisfies a relationship expressed as "the light shield 31>the transparent moisture-resistance material 33>the light-emitting reflector 32".

To achieve such a configuration, in the attaching of the reflector 26 to the cover 24, first, the light shield 31 is stuck on the cover 24 using, for example, an adhesive, as illustrated in FIG. 4A. As illustrated in FIG. 4B, the light-emitting reflector 32 may then be stuck on the light shield 31 using, for example, an adhesive, and the transparent moisture-resistance material 33 may finally be stuck on, for example, the light shield 31 and the light-emitting reflector 32 using, for example, an adhesive in a manner such that the transparent moisture-resistance material 33 covers the light-emitting reflector 32.

In such a configuration, the light shield 31 of the reflector 26 prevents light from the light-emitting reflector 32 from reaching the cover 24. Thus, irrespective of the length of the emission life time period of the light-emitting reflector 32, the medium 1 is prevented from being irradiated with light emitted upon irradiation with excitation light from the light-emitting reflector 32, and light emitted upon irradiation with excitation light from the light-emitting reflector 32 is prevented from being incident on a line sensor of the other line sensor unit. As a result, light from the light-emitting reflector 32 is prevented from adversely affecting image reading while image reading with excitation light and image reading with non-excitation light are being consecutively performed on the medium 1 by repeating an emission of excitation light and non-excitation light from the light-source unit 23.

Figure 5:
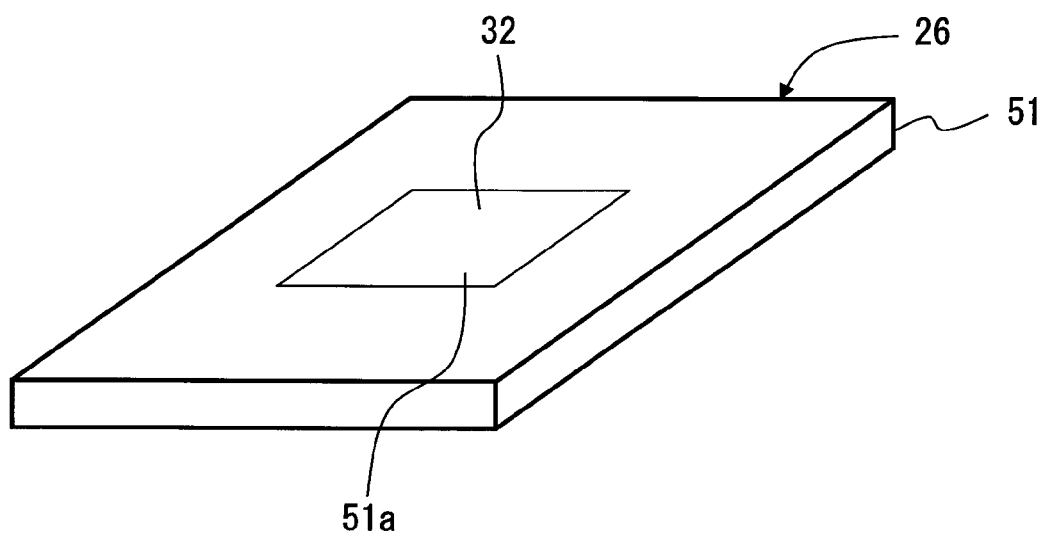
FIG. 5 illustrates a variation of the reflector.

As illustrated in, for example, FIG. 5, the light-emitting reflector 32 may be configured in such a manner that a light shield 51 including a dent 51a shaped in conformity with the size of the light-emitting reflector 32 is provided and the light-emitting reflector 32 is attached within the dent 51a. To protect the light-emitting reflector 32 attached within the dent 51a, a transparent moisture-resistance material may be attached over the light-emitting reflector 32.

FIG. 6A and FIG. 6B illustrate an exemplary configuration in which the images of both sides of a medium are read using the line sensor unit in accordance with the embodiment. FIG. 6A illustrates a front view of line sensor units of the exemplary configuration viewed from an orthogonal direction that is orthogonal to the longer direction of the medium 1; FIG. 6B illustrates a side view of the line sensor units of the exemplary configuration viewed from the longer direction. Images of both sides of a medium 1, which may be a banknote, are read.

The line sensor unit 60 illustrated in FIG. 6A and FIG. 6B includes light guide plates 62 and 67, light source units 63 and 68, a line sensor 65, and a reflector 66 inside a case 61 and a cover 64 provided at an opening 61A of the case 61. From among these elements, the light guide plate 62, the light source unit 63, the line sensor 65, and the reflector 66 are basically the same as the elements of the line sensor unit 20 illustrated in FIG. 2. The reflector 66 includes alight shield 66a, a light-emitting reflector 66b, and a transparent moisture-resistance material 66c. In FIG. 6A and FIG. 6B, the light shields 31 and 66a, the light-emitting reflectors 32 and 66b, and the transparent moisture-resistance materials 33 and 66c of the reflectors 26 and 66 are spaced, but these elements are actually arranged as illustrated in FIG. 3.

The light guide plate 67 and the light source unit 68 are used to read an image with light that passes through the medium 1. The light source unit 68 includes one or more light sources that emit light incident on the light guide plate 67. The light source is, for example, a non-excitation-light source that emits non-excitation light.

As described above, the line sensor unit 20 does not allow light emitted from the light-emitting reflector 32 upon light emission from a non-excitation-light source of the light-source unit 23 to pass through the cover 24, i.e., to escape outside. Similarly, the line sensor unit 60 does not allow light emitted from the light-emitting reflector 66b upon light emission from an excitation-light source of the light-source unit 63 to pass through the cover 64, i.e., to escape outside. Accordingly, the line sensor units 20 and 60 may accurately read an image even when image reading with excitation light and image reading with non-excitation light are consecutively performed on the medium 1.

The configurations illustrated in FIG. 6A and FIG. 6B are applicable to an automatic transaction apparatus with which a transaction can be conducted using banknotes. In the following, an automatic transaction apparatus having the configurations illustrated in FIG. 6A and FIG. 6B, i.e., an automatic transaction apparatus in accordance with the present embodiment, will be described in detail with reference to FIG. 7-FIG. 11.

Figure 8:
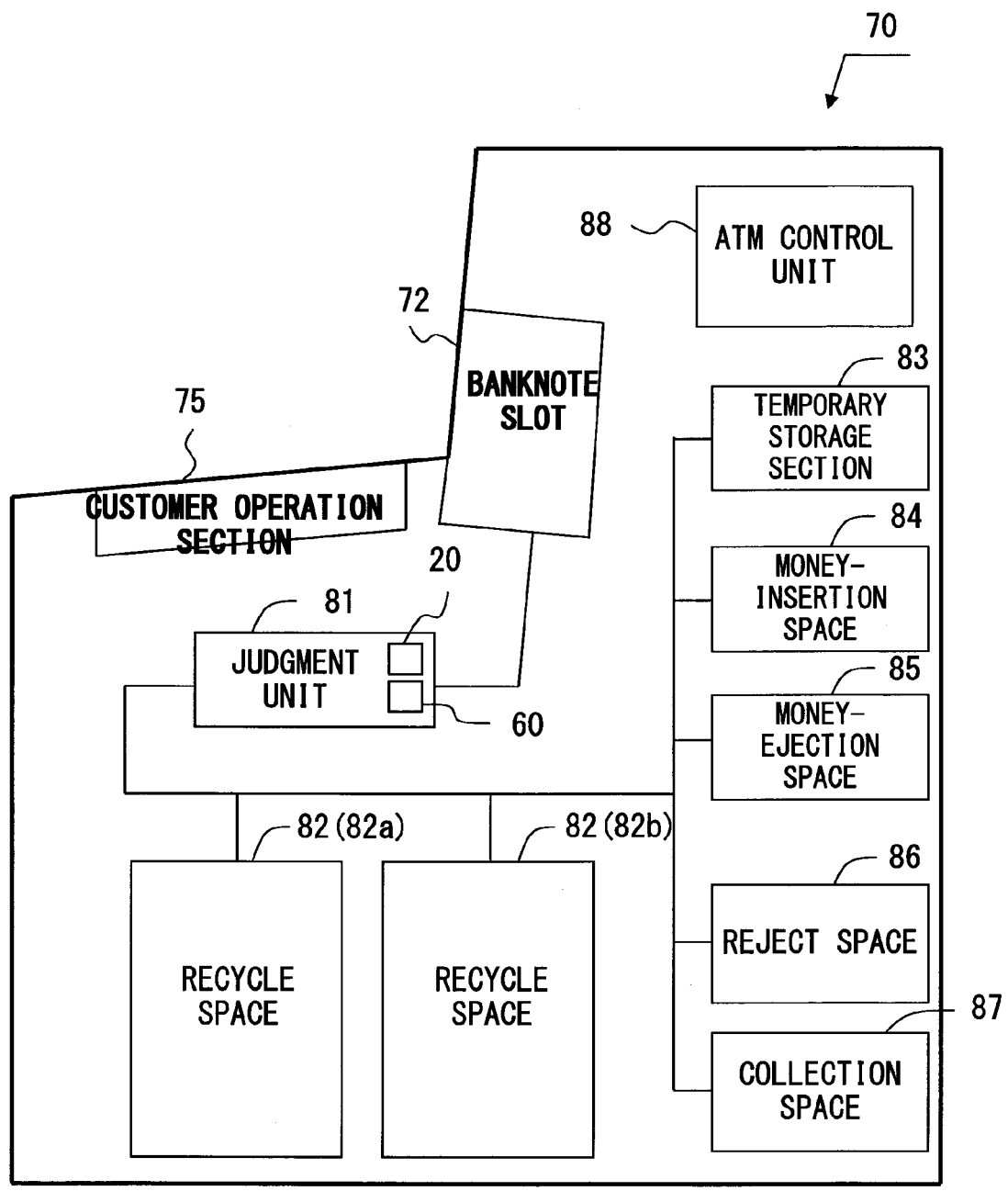
FIG. 8 is an arrangement view of components of the automatic transaction apparatus in accordance with the embodiment.
Figure 9:
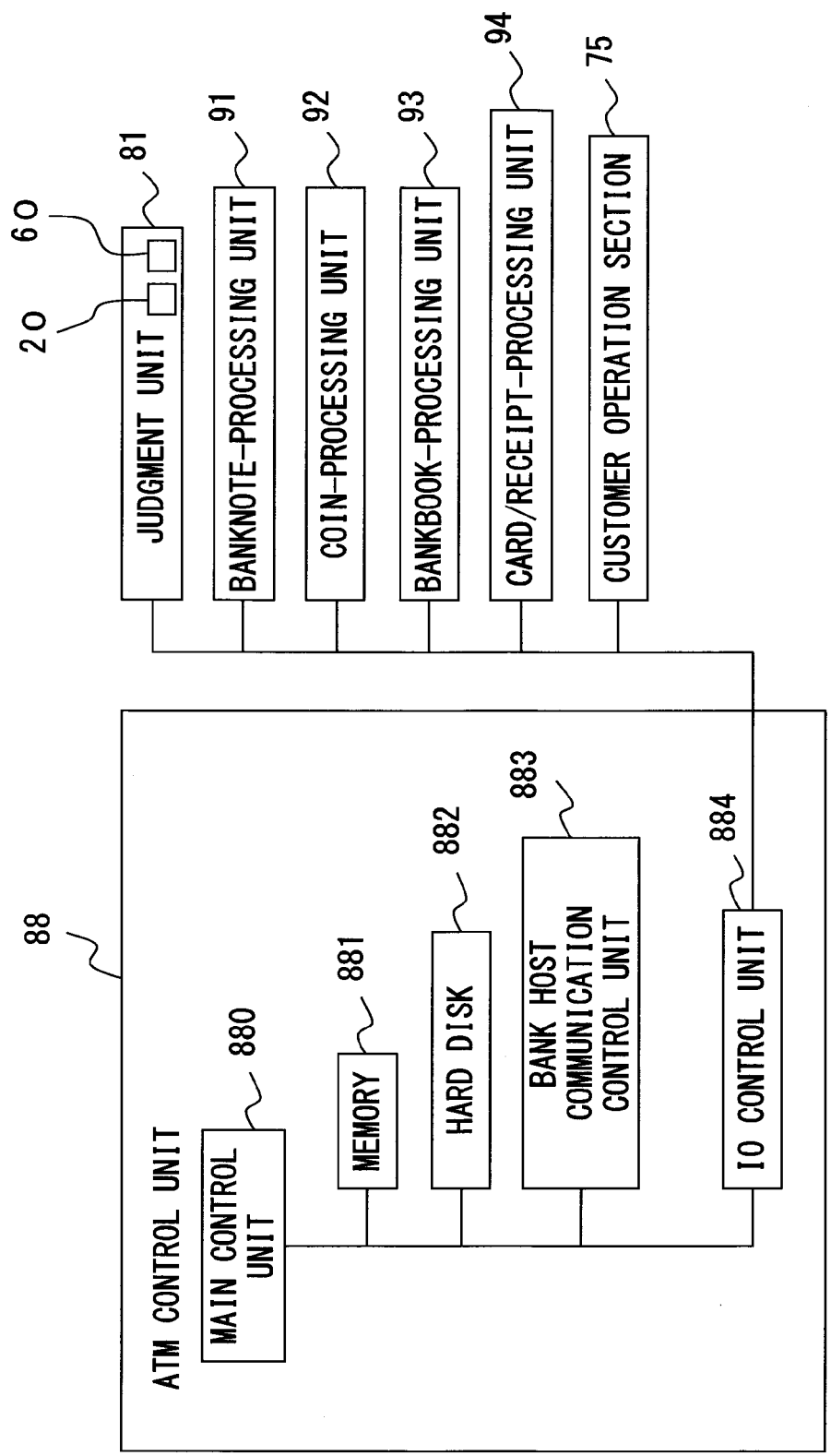
FIG. 9 is a circuit configuration diagram of the automatic transaction apparatus in accordance with the embodiment.

FIG. 7 is an external view of an automatic transaction apparatus in accordance with the embodiment; FIG. 8, an arrangement view of components; FIG. 9, a circuit configuration diagram of the automatic transaction apparatus.

An automatic transaction apparatus 70 in accordance with the embodiment is achieved by applying the present invention to an ATM (Automated Teller Machine) that deals with a banknote as a medium 1. As illustrated in FIG. 7, the automatic transaction apparatus 70 includes: a card slot 71 through which a cash card, a credit card, or the like is inserted or returned and through which a receipt on which details of a conducted transaction has been printed is discharged; a banknote slot 72 through which a banknote is inserted or discharged; a bankbook slot 73 through which a bankbook is inserted or returned; a coin slot 74 through which a coin is inserted or discharged; and a customer operation section 75 provided with a display apparatus and a touch panel. Any automatic transaction apparatus that is capable of reading an image of the medium 1 used in a transaction may be used as the automatic transaction apparatus to which the present invention is applied. Accordingly, the automatic transaction apparatus to which the present invention is applicable is not limited to an ATM.

A judgment unit 81, two recycle spaces 82 (82a and 82b), a temporary storage 83, a money-insertion space 84, a money-ejection space 85, a reject space 86, a collection space 87, and an ATM control unit 88 are provided within the automatic transaction apparatus 70.

The judgment unit 81 magnetically judges whether a banknote is real or false and magnetically judges, for example, damage to, dirt on, and the denomination of the banknote. To optically read the bankbook, the components illustrated in FIG. 6A and FIG. 6B, i.e., the two line sensor units 20 and 60, are provided.

The two recycle spaces 82 are each used to store banknotes of different denominations. The temporary storage 83 is used to temporarily store banknotes to be ejected or inserted. The money-insertion space 84 is used to replenish one of the two recycle spaces 82 with banknotes. The money-ejection space 85 is used to eject banknotes stored in at least one of the two recycle spaces 82. The reject space 86 is used to store a banknote that needs to be returned to a user from among the banknotes inserted in the banknote slot 72. The collection space 87 is used to store a banknote that needs to be collected due to, for example, damage or dirt (a banknote that cannot be recycled in a satisfactory manner). The ATM control unit 88 controls the entirety of the automatic transaction apparatus 70 and achieves a transaction requested by the user via the customer operation section 75.

The ATM control unit 88 is a printed circuit board (PCB) mounted with, for example, various LSI circuits. As illustrated in FIG. 9, a main control unit 880, a memory 881 used by the main control unit 880 for work (actually, the memory 881 is, for example, a memory module), a hard disk apparatus 882, a bank host communication control unit 883, and an IO (Input/Output) control unit 884 are provided. The bank host communication control unit 883 is used to communicate with a host computer (not illustrated).

In addition to the judgment unit 81 and the customer operation section 75, a banknote-processing unit 91, a coin-processing unit 92, a bankbook-processing unit 93, and a card/receipt-processing unit 94 are connected to the IO control unit 884. The elements 91-94 are provided with the following functions.

The banknote-processing unit 91 inserts and ejects banknotes. To insert or eject a banknote, the banknote-processing unit 91 drives, for example, a motor or a solenoid (neither of which is illustrated) that is used to transport the banknote. The coin-processing unit 92 achieves insertion and ejection of coins through the coin slot 74. The bankbook-processing unit 93 transports (receives and returns) a banknote inserted in the bankbook slot 73, reads information written in the bankbook, and prints characters on the bankbook.

The card/receipt-processing unit 94 transports (receives and transports), for example, a cash card or a credit card inserted in the card slot 71, reads information from the inserted card, and provides a receipt on which transaction details are printed. A palm-vein/finger-vein sensor unit 28 is used to read information for biometrics authentication. A terminal stand 27 is provided so that a user can arbitrarily designate a mobile terminal 5 to which key data 6 is distributed.

The judgment unit 81 uses the two line sensor units 20 and 60 so as to read images of both sides of a banknote transmitted from the banknote slot 72 under control of the banknote-processing unit 91, and makes various determinations from the read images, e.g., determines whether the banknote is real or false and determines the denomination of, damage to, and dirt on the banknote. Various results of the determination are reported to the main control unit 880 via the IO control unit 884.

In accordance with the report, the main control unit 880 determines how to deal with the judged banknote and instructs the banknote-processing unit 92 to transport the banknote to a transportation destination to which the banknote is to be transported. As a result, banknotes that have been judged to be true are transported to the temporary storage 83, and banknotes that have not been judged to be true (including banknotes that could not be judged) are transported to the reject section 86. In this way, inserted banknotes are collected in the temporary storage 83 or the reject section 86.

After the collecting is finished, the main control unit 880 displays, on a display apparatus of the customer operation section 75, a screen to inquire as to whether or not the user wishes to conduct a deposit transaction, and the user chooses whether or not to conduct a deposit transaction. The result of the choosing is reported from the customer operation section 75 via the IO control unit 884 to the main control unit 880. Accordingly, when the user chooses to conduct a deposit transaction, the main control unit 880 instructs the banknote-processing unit 91 to transport a banknote collected in the temporary storage 83 to the recycle space 82 that corresponds to the denominator of this banknote. The banknote in the temporary storage 83 that is not to be recycled is transformed to the collection space 87. To return to the user the banknote collected in the reject space 86, this banknote is transported to the banknote slot 72. Meanwhile, when the user does not choose to conduct a deposit transaction, the main control unit 880 instructs the banknote-processing unit 91 to transport the banknotes collected in the temporary storage 83 and the reject space 86 to the banknote slot 72 in order to return these banknotes to the user.

Figure 10:
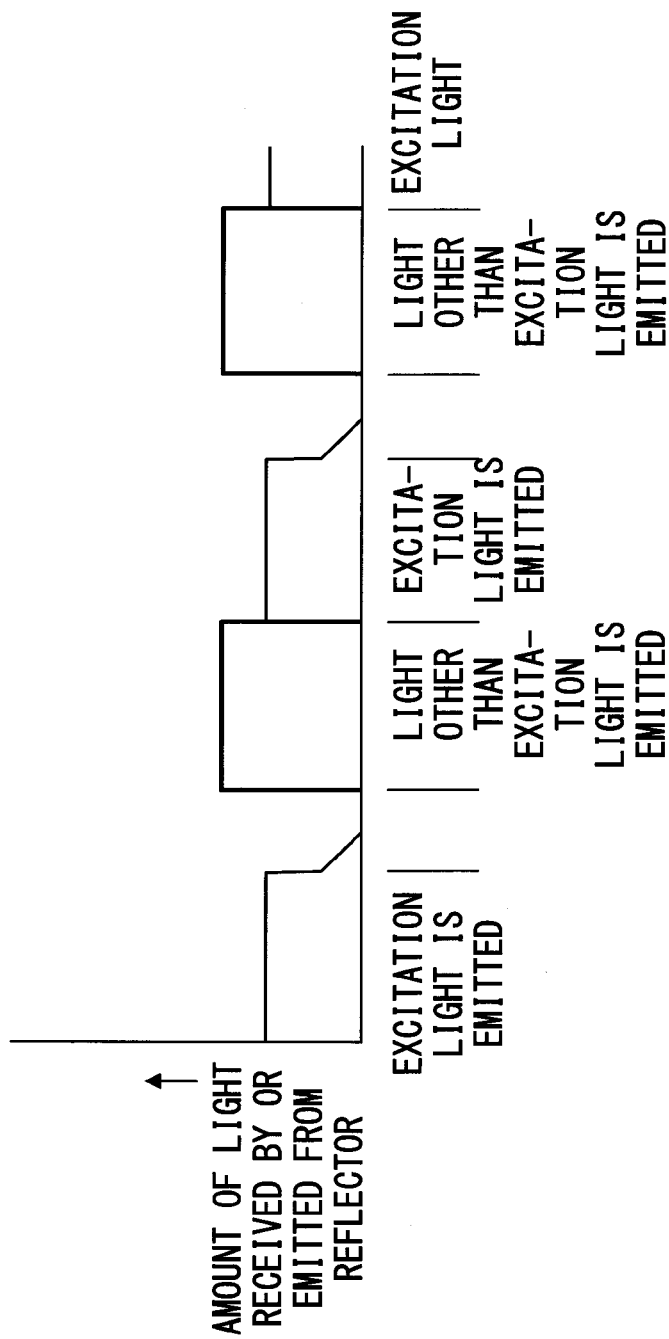
FIG. 10 illustrates a temporal change in the amount of light which is emitted from each light source in the adjusting of requirements to drive each light source and with which a light-emitting reflector is irradiated, and a temporal change in the amount of light which the light-emitting reflector emits upon the irradiation.
Figure 11:
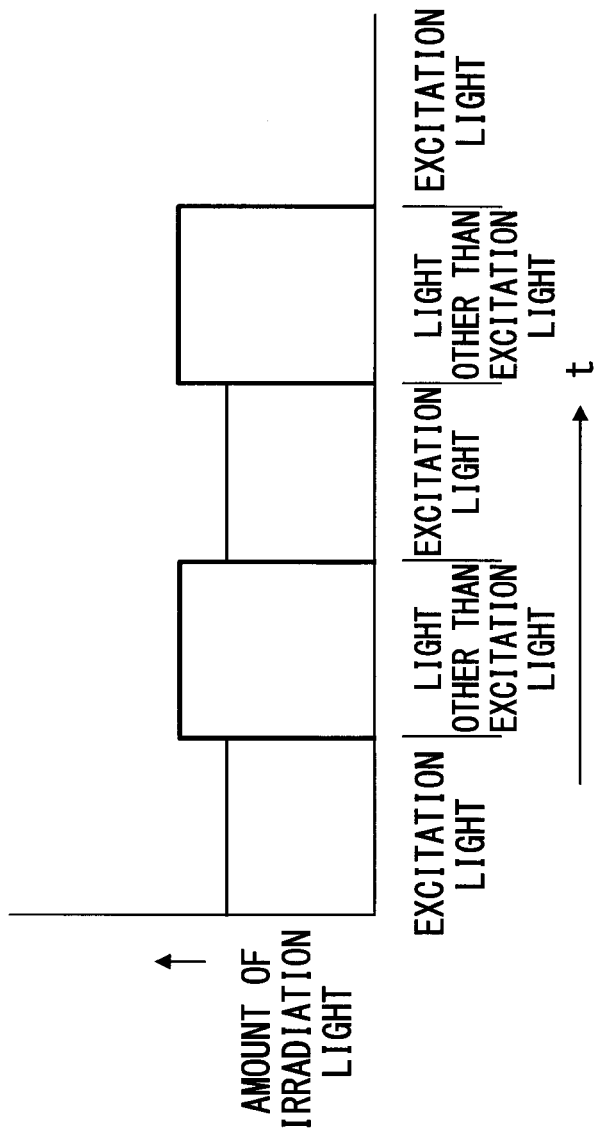
FIG. 11 illustrates a temporal change in the amount of light emitted from each light source to read an image of a medium.

At a preset timing (e.g., activation) or in accordance with an instruction from, for example, a bank worker, the main control unit 880 instructs the judgment unit 81 to cause a light source provided at each of the light source units 23, 63 and 68 of the line sensor units 20 and 60 to emit light so as to adjust requirements to drive the light source. The light source includes an excitation-light source. Accordingly, as illustrated in FIG. 10, after the emission of excitation light ends, the main control unit 880 or the judgment unit 81 waits for the emission life time period of the light-emitting reflector 32 or 66b, which is irradiated with the excitation light, to elapse and then causes non-excitation light (light other than excitation light) to be emitted. As a result, in order to avoid the influence of light emission of the light-emitting reflector 32 or 66b caused by irradiation with excitation light, the requirements to drive the non-excitation-light source are adjusted. In FIG. 10, the horizontal axis corresponds to a time and the vertical axis corresponds to the amount of light. While the light-emitting reflector 32 or 66b is being irradiated with excitation light, the amount of light indicated by the vertical axis corresponds to the amount of irradiation of the irradiation light; while the light-emitting reflector 32 or 66b is not being irradiated with the excitation light, the amount of light indicated by the vertical axis corresponds to the amount of light emitted from the light-emitting reflector 32 or 66b.

As described above, the bad influence of light emitted from the light-emitting reflectors 32 and 66b is eliminated. Accordingly, as illustrated in, for example, FIG. 11, the main control unit 880 causes the light sources provided at the light source units 23, 63 and 68 of the line sensor units 20 and 60 to consecutively emit light and causes the judgment unit 81 to perform image reading with excitation light and image reading with non-excitation light. Thus, once a banknote passes through the judgment unit 81, at least two images, i.e., an image of the banknote read with excitation light and an image of the banknote read with non-excitation light, are obtained. As with FIG. 10, in FIG. 11, the horizontal axis corresponds to a time and the vertical axis corresponds to the amount of light. The amount of light indicated by the vertical axis corresponds to the amount of excitation light or non-excitation light with which the light-emitting reflectors 32 or 66b is irradiated.

In the present embodiment, the light shield that prevents excitation light that is emitted upon irradiation with excitation light from escaping outside is provided at the line sensor unit itself, but the light shield may be provided outside the line sensor unit. The light sources, the line sensors, and so on do not necessarily need to be integrated, and the automatic transaction apparatus may be mounted with preferable elements. Instead of the light-emitting reflector, a member that emits light upon irradiation with excitation light and a member that reflects non-excitation light may be provided. The apparatus mounted with the line sensor unit in accordance with the embodiment is not limited to an automatic transaction apparatus.

As described above, while an image on a medium is being read consecutively with excitation light and non-excitation light by using one line sensor, the disclosed line sensor unit may limit the harmful influence of image reading with excitation light on image reading with non-excitation light.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A line sensor unit comprising:
   a first light source configured to emit excitation light that excites a fluorescent substance;
   a second light source configured to emit non-excitation light that does not excite the fluorescent substance;
   a line sensor configured to receive light from a medium obtained by irradiating the medium with the excitation light or the non-excitation light;
   a light-emitting unit, which is excited upon receipt of the excitation light, configured to emit light responsive to the excitation light, the emitted light being incident on the line sensor; and
   a light-shielding unit, which is provided on a side opposite to a line-sensor side of the light-emitting unit, configured to block light advancing from the light-emitting unit to the medium.

2. The line sensor unit according to claim 1, wherein the light-emitting unit reflects and causes the non-excitation light to be incident on the line sensor.

3. An automatic transaction apparatus that allows a user to conduct a transaction using a medium, the automatic transaction apparatus comprising:
   a first light source configured to emit excitation light that excites a fluorescent substance;
   a second light source configured to emit non-excitation light that does not excite the fluorescent substance;
   a line sensor configured to receive light from a medium obtained by irradiating the medium with the excitation light or the non-excitation light for the transaction;
   a light-emitting unit, which is excited upon receipt of the excitation light, configured to emit light responsive to the excitation light, the emitted light being incident on the line sensor; and
   a light-shielding unit, which is provided on a side opposite to a line-sensor side of the light-emitting unit, configured to block light advancing from the light-emitting unit to the medium.

4. The automatic transaction apparatus according to claim 3, wherein the light-emitting unit reflects and causes the non-excitation light to be incident on the line sensor.

* * * * *